(12) United States Patent
Hogan et al.

(10) Patent No.: US 6,376,186 B1
(45) Date of Patent: Apr. 23, 2002

(54) POLYNUCLEOTIDE PROBES FOR DETECTION AND QUANTITATION OF STAPHYLOCOCCUS

(75) Inventors: James J. Hogan, Coronado; Patricia Gordon, San Diego, both of CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 09/565,241

(22) Filed: May 3, 2000

Related U.S. Application Data

(60) Provisional application No. 60/132,409, filed on May 3, 1999.

(51) Int. Cl.$^7$ ............................ C12Q 1/68; C07H 21/04
(52) U.S. Cl. ...................... 435/6; 536/23.7; 536/24.32; 435/810
(58) Field of Search .................. 435/6, 810; 536/24.32, 536/23.7

(56) References Cited

U.S. PATENT DOCUMENTS

| | | | |
|---|---|---|---|
| 4,851,330 A | 7/1989 | Kohne | 435/6 |
| 5,030,557 A | 7/1991 | Hogan et al. | 435/6 |
| 5,185,439 A | 2/1993 | Arnold, Jr. et al. | 536/24.3 |
| 5,283,174 A | 2/1994 | Arnold, Jr. et al. | 435/6 |
| 5,364,763 A | 11/1994 | Kacian | 435/7.32 |
| 5,374,522 A | 12/1994 | Murphy et al. | 435/6 |
| 5,514,551 A * | 5/1996 | Yang et al. | 435/6 |
| 5,539,082 A | 7/1996 | Nelson et al. | 530/300 |
| 5,541,308 A | 7/1996 | Hogan et al. | 536/23.1 |
| 5,582,975 A | 12/1996 | Milliman | 435/6 |
| 5,591,578 A | 1/1997 | Meade et al. | 435/6 |
| 5,620,847 A | 4/1997 | Greisen et al. | 435/6 |
| 5,635,348 A | 6/1997 | Leong | 435/6 |
| 5,635,367 A | 6/1997 | Lund | 435/34 |
| 5,656,207 A | 8/1997 | Woodhead et al. | 252/700 |
| 5,681,698 A | 10/1997 | Hogan et al. | 435/6 |
| 5,708,160 A | 1/1998 | Goh et al. | 536/24.32 |
| 5,714,321 A | 2/1998 | Hogan | 435/6 |
| 5,770,369 A | 6/1998 | Meade et al. | 435/6 |
| 5,824,518 A | 10/1998 | Kacian et al. | 435/91.21 |
| 5,837,452 A | 11/1998 | Clark et al. | 435/6 |
| 5,849,488 A | 12/1998 | Alatossava et al. | 435/6 |
| 5,945,286 A | 8/1999 | Krihak et al. | 435/6 |
| 5,952,202 A | 9/1999 | Aoyagi et al. | 435/91.2 |
| 5,998,135 A | 12/1999 | Rabbani et al. | 435/6 |
| 6,031,091 A | 2/2000 | Arnold, Jr. et al. | 536/25.34 |

FOREIGN PATENT DOCUMENTS

| | | |
|---|---|---|
| EP | 0318245 | 5/1989 |
| EP | 0639649 | 2/1995 |
| EP | 0786519 | 7/1997 |
| EP | 0808907 | 11/1997 |
| JP | 7255486 | 10/1995 |
| WO | 9641878 | 12/1996 |
| WO | 9820162 | 5/1998 |
| WO | 9857158 | 12/1998 |
| WO | 9857159 | 12/1998 |
| WO | 0066789 | 11/2000 |

OTHER PUBLICATIONS

Greisen, K. et al. Journal of Clinical Microbiology 32(2):335–351, Feb. 1994.*

Arnold et al., "Assay Formats Involving Acridinum–Ester–Labeled DNA Probes", *Clin. Chem.*, 35(8):1588–1594 (1989).

Barone et al., "In situ activation of bis–dialkylaminophosphines—a new method for synthesizing deoxyoligonucleotides on polymer supports", *Nuc. Acids Res.*, 12(10):4051–4061 (1984).

Lane et al., "Rapid determination of 16S ribosomal RNA sequences for phylogenetic analyses", *Proc. Natl. Acad Sci. USA*, 82:6955–6959 (1985).

Sambrook et al., *Molecular Cloning—A Laboratory Manual*, 2nd Ed., vol. 2, Chpt. 9, "Analysis and Cloning of Eukaryotic Genomic DNA"; Chpt. 10, "Preparation of Radiolabeled DNA and RNA Probes"; and Chpt. 11, "Synthetic Oligonucleotide Probes", 1989.

Kloos et al., "Staphylococcus and Micrococcus", *Manual of Clin. Microbiol.*, 6th Ed., P.R. Murray et al., eds., chpt. 22:282–298 (1995).

\* cited by examiner

*Primary Examiner*—Carla J. Myers
*Assistant Examiner*—Diana Johannsen
(74) *Attorney, Agent, or Firm*—Michael J. Gilly

(57) ABSTRACT

Polynucleotide probes and accessory helper oligonucleotides useful for detecting bacteria that are members of the genus Staphylococcus. The hybridization probes are highly specific for Staphylococcal bacteria and do not cross-hybridize with the rRNA or rDNA of numerous other bacterial and fungal species.

25 Claims, 1 Drawing Sheet

STAPH.GENUS

*S.epidermidis* SEQ ID NO:12

--AGCGAAACCGCGAGGUCAAGC------AAAUCCCAUAAAGUUGUUCUCAGUUCGGAUUGUAGUCUGCAACUCGACUAUAUGAAGCUGGAAUCGCUAGU

*Staph.aureus* SEQ ID NO:13

--AGCGAAACCGCGAGGUCAAGC------AAAUCCCAUAAAGUUGUUCUCAGUUCGGAUUGUAGUCUGCAACUCGACUACAUGAAGCUGGAAUCGCUAGU

OmeSauA1259(-) SEQ ID NO:2

(3')GCUUUGGCGCUCCAGUU(5')

SauA1276(-) SEQ ID NO:1

(3')CG------TTTAGGGTATTTCAACAAGAGTCAAGCC(5')

SauA1306(-) SEQ ID NO:3

(3')TAACATCAGACGTTGAGCTGATGTACTTCGACCTTAGCG(5')

NON.TARGET

*E.coli* SEQ ID NO:14

--AGCGACCUCGCGAGAGCAAGC------GGACCUCAUAAAGUGCGUCGUAGUCCGGAUUGGAGUCUGCAACUCGACUCCAUGAAGUCGGAAUCGCUAGU

*S.bovis* SEQ ID NO:15

--CGCGAGUCGGUGACGGCAAGC------AAAUCUCUUAAAGCCAAUCUCAGUUCGGAUUGUAGGCUGCAACUCGCCUACAUGAAGUCGGAAUCGCUAGU

*S.pneumoniae* SEQ ID NO:16

--CGCAAGCCGGUGACGGCAAGC------UAAUCUCUUAAAGCCAGUCUCAGUUCGGAUUGUAGGCUGCAACUCGCCUACAUGAAGUCGGAAUCGCUAGU

*S.agalactiae* SEQ ID NO:17

--CGCAAGCCGGUGACGGCAAGC------UAAUCUCUUAAAGCCAAUCUCAGUUCGGAUUGUAGGCUGCAACUCGCCUACAUGAAGUCGGAAUCGCUAGU

*S.sanguis* SEQ ID NO:18

--CGCAAGCCGGUGACGGCAAGC------UAAUCUCUGAAAGCCAGUCUCAGUUCGGAUUGUAGGCUGCAACUCGCCUACAUGAAGUCGGAAUCGCUAGU

*S.cerevisiae* SEQ ID:19

GGCCGAGAGGUCUUGGUAAUCUUGUGAAACUCCGUCGUGCUGGGGAUAGAGCAUUGUAAUUAUUGCUCUUCAACGAGGAAUUCCUAGUAAGCGCAAGUCA

*Cand.albicans* SEQ ID NO:20

---AUAAGCCUUGGCCGAGAGGUCUGGGAAAUCUUGUGAAACUCCGUCGUGCUGGGGAUAGAGCAUUGUAAUUGUUGCUCUUCAACGAGGAAUUCCUAGU

POLYNUCLEOTIDE PROBES FOR DETECTION AND QUANTITATION OF STAPHYLOCOCCUS

RELATED APPLICATIONS

This application claims the benefit of U.S. Provisional Application No. 60/132,409, filed May 3, 1999. The disclosure of this related application is hereby incorporated by reference.

FIELD OF THE INVENTION

The present invention relates to nucleic acid detection systems. More specifically, the invention relates to polynucleotide probes having binding specificity for rRNA or rDNA of bacteria that are members of the genus Staphylococcus.

BACKGROUND OF THE INVENTION

Bacteria among the genus Staphylococcus are classified as members of the broad Bacillus-Lactobacillus-Streptococcus cluster. The closest phylogenetic relatives of the genus Staphylococcus include the genera Bacillus, Bronchothrix, Enterococcus, Listeria and Planococcus. Staphylococcal bacteria are non-motile, gram-positive cocci having genomic molar percentages of guanine and cytosine (G+C) in the range of from to 39%. These bacteria commonly are found on skin and mucosal surfaces of humans. Notably, these organisms can become opportunistic pathogens following trauma to the skin. Indeed, S. aureus is frequently associated with infections of the skin. Infections of wounds and deep tissue with this Staphylococcal species can become life-threatening.

It is well established that two single strands of deoxyribonucleic acid ("DNA") or ribonucleic acid ("RNA") can associate or "hybridize" with one another to form a double-stranded structure having two strands held together by hydrogen bonds between complementary base pairs. The individual strands of nucleic acid are formed from nucleotides that comprise the bases: adenine (A), cytosine (C), thymine (T), guanine (G), uracil (U) and inosine (I). In the double helical structure of nucleic acids, the base adenine hydrogen bonds with the base thymine or uracil, the base guanine hydrogen bonds with the base cytosine and the base inosine hydrogen bonds with adenine, cytosine or uracil. At any point along the chain, therefore, one may find the classical "Watson-Crick" base pairs A:T or A:U, T:A or U:A, and G:C or C:G. However, one may also find A:G, G:U and other "wobble" or mismatched base pairs in addition to the traditional ("canonical") base pairs.

A double-stranded nucleic acid hybrid will result if a first single-stranded polynucleotide is contacted under hybridization-promoting conditions with a second single-stranded polynucleotide having a sufficient number of contiguous bases complementary to the sequence of the first polynucleotide. DNA/DNA, RNA/DNA or RNA/RNA hybrids may be formed under appropriate conditions.

Generally, a probe is a single-stranded polynucleotide having some degree of complementarity with the nucleic acid sequence that is to be detected ("target sequence"). Probes commonly are labeled with a detectable moiety such as a radioisotope, an antigen or a chemiluminescent moiety.

Descriptions of nucleic acid hybridization as a procedure for detecting particular nucleic acid sequences are given by Kohne in U.S. Pat. No. 4,851,330, and by Hogan et al., in U.S. Pat. Nos. 5,541,308 and 5,681,698. These references also describe methods for determining the presence of RNA-containing organisms in a sample which might contain such organisms. These procedures require probes that are sufficiently complementary to the ribosomal RNA (rRNA) of one or more non-viral organisms or groups of non-viral organisms. According to the method, nucleic acids from a sample to be tested and an appropriate probe are first mixed and then incubated under specified hybridization conditions. Conventionally, but not necessarily, the probe will be labeled with a detectable label. The resulting hybridization reaction is then assayed to detect and quantitate the amount of labeled probe that has formed duplex structures in order to detect the presence of rRNA contained in the test sample.

With the exception of viruses, all prokaryotic organisms contain rRNA genes encoding homologs of the procaryotic 5S, 16S and 23S rRNA molecules. In eucaryotes, these rRNA molecules are the 5S rRNA, 5.8S rRNA, 18S rRNA and 28S rRNA which are substantially similar to the prokaryotic molecules. Probes for detecting specifically targeted rRNA subsequences in particular organisms or groups of organisms in a sample have been described previously. These highly specific probe sequences advantageously do not cross react with nucleic acids from any other bacterial species or infectious agent under appropriate stringency conditions.

The present invention provides polynucleotide probes that can be used to detect the members of the genus Staphylococcus in a highly specific manner.

SUMMARY OF THE INVENTION

One aspect of the present invention relates to an oligonucleotide probe that specifically hybridizes a Staphylococcal nucleic acid target region corresponding to E. coli 16S rRNA nucleotide positions 1276–1305 under a high stringency hybridization condition to form a detectable probe:target duplex. The oligonucleotide probe has a length of up to 100 nucleotides and includes at least 17 contiguous nucleotides contained within the sequence of SEQ ID NO:10. In a preferred embodiment, the oligonucleotide probe includes at least 30 contiguous nucleotides contained within the sequence of SEQ ID NO:10. The high stringency hybridization condition may be provided by either: (a) 0.48 M sodium phosphate buffer, 0. 1% sodium dodecyl sulfate, and 1 mM each of EDTA and EGTA, or (b) 0.6 M LiCl, 1% lithium lauryl sulfate, 60 mM lithium succinate and 10 mM each of EDTA and EGTA. The oligonucleotide probe may be made of DNA, but also may include at least one nucleotide analog. For example, the nucleotide analog may include a methoxy group at the 2' position of a ribose moiety. In one embodiment the invented oligonucleotide probe has the sequence of any one of SEQ ID NO:1 or the complement thereof, SEQ ID NO:2 or the complement thereof, and SEQ ID NO:3 or the complement thereof. In a preferred embodiment, the sequence of the oligonucleotide is given by SEQ ID NO:2 or SEQ ID NO:3, and the oligonucleotide is a helper oligonucleotide. Any of the disclosed oligonucleotides can include a detectable label. Particular examples of detectable labels include chemiluminescent labels and radio-labels. In another preferred embodiment, the oligonucleotide probe has a sequence given by SEQ ID NO:1, and further includes a detectable label. A highly preferred detectable label is an acridinium ester.

Another aspect of the present invention relates to a probe composition for detecting nucleic acids of bacteria that are members of the Staphylococcus genus. This composition includes an oligonucleotide probe that hybridizes under a high stringency condition to a Staphylococcal target region corresponding to *E. coli* 16S rRNA nucleotide positions 1276–1305 to form a detectable probe:target duplex. This oligonucleotide probe has a length of up to 100 nucleotide bases and includes at least 30 contiguous nucleotides contained within the sequence of SEQ ID NO:10 or the complement thereof. Under high stringency hybridization conditions the oligonucleotide probe specifically hybridizes nucleic acids present in *Staphylococcus aureus, Staphylococcus cohnii, Staphylococcus delphi, Staphylococcus epidermidis, Staphylococcus haemolyticus, Staphylococcus hominis, Staphylococcus hyicus, Staphylococcus intermedius, Staphylococcus saprophyticus, Staphylococcus simulan* and *Staphylococcus warneri*. In certain embodiments, the oligonucleotide probe is made of DNA. Exemplary high stringency hybridization conditions are provided by either: (a) 0.48 M sodium phosphate buffer, 0.1% sodium dodecyl sulfate, and 1 mM each of EDTA and EGTA, or (b) 0.6 M LiCl, 1% lithium lauryl sulfate, 60 mM lithium succinate and 10 mM each of EDTA and EGTA. In a highly preferred embodiment, the oligonucleotide probe includes the sequence of SEQ ID NO:1 or the complement thereof. In another highly preferred embodiment, the length of the oligonucleotide probe is up to 60 bases. In and even more highly preferred embodiment of the invention, the oligonucleotide probe has the length and sequence of SEQ ID NO:1. Certain embodiments of the invented probe composition further include a detectable label on the oligonucleotide probe. For example, when the oligonucleotide probe has a length of up to 60 nucleotides, the probe may include a detectable label. Alternatively, when the probe has the length and sequence of SEQ ID NO:1 there can be included a detectable label. Regardless of whether the probe composition includes a labeled oligonucleotide probe of from 17–100 nucleotides in length, or from 17–60 nucleotides in length, or having the length and sequence of SEQ ID NO:1 the detectable label may be a chemiluminescent label, such as an acridinium ester, or a radiolabel. It is preferred that the invented probe composition include at least one helper oligonucleotide that facilitates formation of the detectable probe:target duplex under high stringency hybridization conditions. These helper oligonucleotides may include at least one nucleotide analog, such as a ribose moiety having a methoxy group disposed at the 2' position. In a highly preferred embodiment of the invented probe composition, the helper oligonucleotide has a sequence given by SEQ ID NO:2 or SEQ ID NO:3.

Yet another aspect of the invention relates to a method for detecting the presence of Staphylococcus bacteria in a test sample. This method involves steps for providing to the test sample a probe composition that includes an oligonucleotide probe that hybridizes under a high stringency condition to a Staphylococcal target region corresponding to *E. coli* 16S rRNA nucleotide positions 1276–1305 to form a detectable probe:target duplex. The oligonucleotide probe has a length of up to 100 nucleotide bases and includes at least 17, or more preferably at least 30 contiguous nucleotides contained within the sequence of SEQ ID NO:10 or the complement thereof. Under high stringency hybridization conditions the oligonucleotide probe specifically hybridizes nucleic acids present in *Staphylococcus aureus, Staphylococcus cohnii, Staphylococcus delphi, Staphylococcus epidermis, Staphylococcus haemolyticus, Staphylococcus hominis, Staphylococcus hyicus, Staphylococcus intermedius, Staphylococcus saprophyticus, Staphylococcus simulan* and *Staphylococcus warneri*. Thereafter, the resulting mixture is hybridized under high stringency conditions so that any nucleic acids from Staphylococcus bacteria that may be present in the test sample form probe:target duplexs with the probe oligonucleotide. Finally, the method involves detecting the probe:target duplexs as an indicator of the presence of Staphylococcus bacteria in the test sample. In one embodiment of the invented method the test sample includes bacteria, and there is conducted a preliminary step for releasing nucleic acids from any bacteria that may be present in said test sample. In a different embodiment of the method the test sample is a lysate. In general, high stringency hybridization conditions can be provided by either: (a) 0.48 M sodium phosphate buffer, 0.1% sodium dodecyl sulfate, and 1 mM each of EDTA and EGTA, or (b) 0.6 M LiCl, 1% lithium lauryl sulfate, 60 mM lithium succinate and 10 nM each of EDTA and EGTA. However, it is to be understood that other high stringency hybridization conditions can give good results. In a preferred embodiment, the oligonucleotide probe has the length and sequence of SEQ ID NO:1, and optionally may include a detectable label. This detectable label may be an acridinium ester. When this is the case the detecting step in the invented method may include a step for performing luminometry to detect any of the probe:target duplexs that are formed during the hybridization step. When the oligonucleotide probe has the length and sequence of SEQ ID NO:1, the probe composition may further include at least one helper oligonucleotide that facilitates formation of the probe:target duplex. Highly preferred helper oligonucleotides have the sequences of SEQ ID NO:2 and SEQ ID NO:3.

Still yet another aspect of the invention relates to a kit that can be used for detecting the presence in a test sample of nucleic acids from bacteria that are members of the Staphylococcus genus. The kit contains a probe composition that includes an oligonucleotide probe that hybridizes under a high stringency condition to a Staphylococcal target region corresponding to *E. coli* 16S rRNA nucleotide positions 1276–1305 to form a detectable probe:target duplex. The oligonucleotide probe has a length of up to 100 nucleotide bases and includes at least 30 contiguous nucleotides contained within the sequence of SEQ ID NO:10 or the complement thereof. Under high stringency hybridization conditions the oligonucleotide probe specifically hybridizes nucleic acids present in *Staphylococcus aureus, Staphylococcus cohnii, Staphylococcus delphi, Staphylococcus epidermidis, Staphylococcus haemolyticus, Staphylococcus hominis, Staphylococcus hyicus, Staphylococcus intermedius, Staphylococcus saprophyticus, Staphylococcus simulan* and *Staphylococcus warneri*. Also included in the kit are printed instructions specifying, in order of implementation, the steps to be followed for detecting nucleic acids from bacteria that are members of the Staphylococcus genus by detecting a complex between the oligonucleotide probe and a Staphylococcus nucleic acid target. Both the probe composition and the printed instructions are in packaged combination with each other.

Definitions

As used herein, the following terms have the given meanings unless expressly stated to the contrary.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. For a 5'-nucleotide, the sugar contains a hydroxyl group (—OH) at the 5'-carbon-5. The term also includes analogs of such subunits, such as a methoxy group at the 2' position of the ribose (OMe). As used herein, methoxy oligonucleotides containing "T" residues have a methoxy group at the 2' position of the ribose moiety, and a uracil at the base position of the nucleotide.

A "non-nucleotide unit" is a unit which does not significantly participate in hybridization of a polymer. Such units must not, for example, participate in any significant hydrogen bonding with a nucleotide, and would exclude units having as a component one of the five nucleotide bases or analogs thereof.

An "oligonucleotide" is a nucleotide polymer having two or more nucleotide subunits covalently joined together. Oligonucleotides are generally about 10 to about 100 nucleotides in length. The sugar groups of the nucleotide subunits may be ribose, deoxyribose, or modified derivatives thereof such as OMe. The nucleotide subunits may by joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage.

Nitrogenous base analogs also may be components of oligonucleotides in accordance with the invention.

A "target nucleic acid" is a nucleic acid comprising a target nucleic acid sequence.

A "target nucleic acid sequence," "target nucleotide sequence" or "target sequence" is a specific deoxyribonucleotide or ribonucleotide sequence that can be hybridized by an oligonucleotide.

An "oligonucleotide probe" is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promotor sequences, restriction endonuclease recognition sites, or sequences that confer a desired secondary or tertiary structure such as a catalytic active site can be used to facilitate detection using the invented probes. An oligonucleotide probe optionally may be labeled with a detectable moiety such as a radioisotope, a fluorescent moiety, a chemiluminescent moiety, an enzyme or a ligand, which can be used to detect or confirm probe hybridization to its target sequence. Oligonucleotide probes are preferred to be in the size range of from 10 to 100 nucleotides in length.

A "detectable moiety" is a molecule attached to, or synthesized as part of, a nucleic acid probe. This molecule should be uniquely detectable and will allow the probe to be detected as a result. These detectable moieties are often radioisotopes, chemiluminescent molecules, enzymes, haptens, or even unique oligonucleotide sequences.

A "hybrid" or a "duplex" is a complex formed between two single-stranded nucleic acid sequences by Watson-Crick base pairings or non-canonical base pairings between the complementary bases.

"Hybridization" is the process by which two complementary strands of nucleic acid combine to form a double-stranded structure ("hybrid" or "duplex").

"Complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or uracil (U), while guanine (G) ordinarily complements cytosine (C).

"Mismatch" refers to any pairing, in a hybrid, of two nucleotides which do not form canonical Watson-Crick hydrogen bonds. In addition, for the purposes of the following discussions, a mismatch can include an insertion or deletion in one strand of the hybrid which results in an unpaired nucleotide(s).

The term "stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid. Exemplary high stringency conditions are provided in the working Examples.

The term "probe specificity" refers to a characteristic of a probe which describes its ability to distinguish between target and non-target sequences.

The term "variable region" refers to a nucleotide polymer which differs by at least one base between the target organism and non-target organisms contained in a sample.

A "conserved region" is a nucleic acid subsequence which is not variable between at least two different polynucleotides.

"Bacteria" are members of the phylogenetic group eubacteria, which is considered one of the three primary kingdoms.

The term "sequence divergence" refers to a process by which nucleotide polymers become less similar during evolution.

The term "sequence convergence" refers to a process by which nucleotide polymers become more similar during evolution.

"Tm" refers to the temperature at which 50% of the probe is converted from the hybridized to the unhybridized form.

A "helper oligonucleotide" is an oligonucleotide that binds a region of a target nucleic acid other than the region that is bound by an oligonucleotide probe. Helper oligonucleotides impose new secondary and tertiary structures on the targeted region of the single-stranded nucleic acid so that the rate of binding of the oligonucleotide probe is accelerated. Although helper oligonucleotides are not labeled with a detectable label when used in conjunction with labeled oligonucleotide probes, they facilitate binding of labeled probes and so indirectly enhance hybridization signals.

The phrases "consist essentially of" or "consisting essentially of" means that the oligonucleotide has a nucleotide sequence substantially similar to a specified nucleotide sequence. Any additions or deletions are non-material variations of the specified nucleotide sequence which do not prevent the oligonucleotide from having its claimed property, such as being able to preferentially hybridize under high stringency hybridization conditions to its target nucleic acid over non-target nucleic acids.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from 100% to 80% or from 0 base mismatches in a 10 nucleotide target sequence to 2 bases mismatched in a 10 nucleotide target sequence. In preferred embodiments, the percentage is from 100% to 85%. In more preferred embodiments this percentage is from 90% to 100%; in other preferred embodiments, this percentage is from 95% to 100%.

By "sufficiently complementary" or "substantially complementary" is meant nucleic acids having a sufficient amount of contiguous complementary nucleotides to form, under high stringency hybridization conditions, a hybrid that is stable for detection.

By "nucleic acid hybrid" or "probe:target duplex" is meant a structure that is a double-stranded, hydrogen-bonded structure, preferably 10 to 100 nucleotides in length, more preferably 14 to 50 nucleotides in length. The structure is sufficiently stable to be detected by means such as chemiluminescent or fluorescent light detection, autoradiography, electrochemical analysis or gel electrophoresis. Such hybrids include RNA:RNA, RNA:DNA, or DNA:DNA duplex molecules.

By "negative sense" is meant a nucleic acid molecule perfectly complementary to a reference (i.e., sense) nucleic acid molecule.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

By "preferentially hybridize" is meant that under high stringency hybridization conditions oligonucleotide probes can hybridize their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of bacteria in the Staphylococcus genus and distinguish their presence from that of other organisms. Preferential hybridization can be measured using techniques known in the art and described herein. For example, when compared with hybridization to *C. albicans* nucleic acids, oligonucleotide probes of the invention preferentially hybridize nucleic acids from bacteria in the Staphylococcus genus by about 500–3,000 fold.

A "target nucleic acid sequence region" of bacteria in the Staphylococcus genus refers to a nucleic acid sequence present in nucleic acid or a sequence complementary thereto found in Staphylococcal bacteria, which is not present in nucleic acids of other species. Nucleic acids having nucleotide sequences complementary to a target sequence may be generated by target amplification techniques such as polymerase chain reaction (PCR) or transcription mediated amplification (e.g., Kacian and Fultz, Nucleic Acid Sequence Amplification Methods, U.S. Pat. No. 5,824,518).

BRIEF DESCRIPTION OF THE DRAWINGS

FIG. 1 shows the sequences of one oligonucleotide probe and two helper oligonucleotides aligned with the sequences of some members of the positively reacting species and non-phylogenetically related species that will not hybridize with the invented probes.

DETAILED DESCRIPTION OF THE INVENTION

Herein we disclose preferred target nucleotide sequences for oligonucleotide probes and helper oligonucleotides that can be used to detect and identify the rRNA or rDNA of bacteria that are members of the genus Staphylococcus. Highly preferred polynucleotide probes and accessory helper oligonucleotides that are useful for specifically detecting these bacteria are particularly disclosed. The probes, which are complementary to particular rRNA sequences of the 16S rRNA, advantageously are capable of distinguishing Staphylococcus organisms from the known phylogenetically nearest neighbors.

In addition to having nucleic acid sequences that permit hybridization to the ribosomal RNA (rRNA) or DNA (rDNA) sequences of Staphylococcal organisms, the oligonucleotide probes of the invention are at least 90% complementary, preferably perfectly complementary, to at least a portion of the described target sequence region identified by SEQ ID NO:11. The portion is at least 17 nucleotides in length, still more preferably at least 30 nucleotides in length and still more preferably at least 39 nucleotides in length.

As indicated above, the invented oligonucleotides are targeted to nucleic acid sequences of Staphylococcal organisms. These oligonucleotides can be used as probes that preferentially hybridize to a nucleic acid target region to form a detectable duplex that indicates the presence of a Staphylococcal organism. Alternatively, the invented oligonucleotides can be used as helper oligonucleotides that hybridize to a nucleic acid target region present in these bacteria under high stringency hybridization conditions, and that can enhance the formation of a duplex between a labeled oligonucleotide probe and its complementary target nucleic acid.

In preferred embodiments, the oligonucleotide probes described herein selectively hybridize nucleic acids from Staphylococcal organisms over those from other organisms under high stringency hybridization conditions. In some embodiments of the present invention, the oligonucleotide probe comprises a detectable moiety, such as an acridinium ester or a radioisotope.

Preferred methods for detecting the presence of Staphylococcal organisms include the step of contacting a test sample under high stringency hybridization conditions with an oligonucleotide probe that preferentially hybridizes to a target nucleic acid of Staphylococcal organisms over a nucleic acid sequence of other organisms. The target ribosomal nucleic acid sequence contained in rRNA of bacteria in the genus Staphylococcus has the sequence given by SEQ ID NO:11. Preferred probes for detecting the rRNA of bacteria in the genus Staphylococcus have sequences of up to 100 nucleotides in length and have at least 17 contiguous nucleotides, more preferably 30 contiguous nucleotides, and still more preferably 39 contiguous nucleotides contained in the sequence given by GCGATTCCAGCTTCATGTAGTC-GAGTTGCAGACTACAATCCGAACT-GAGAACAACTTTATGGGATTTGCTTGAC-CTCGCGGTTTCG (SEQ ID NO:10). However, useful probes for hybridizing rDNA have sequences of up to 100 nucleotides in length and have at least 17 contiguous nucleotides, more preferably 30 contiguous nucleotides, and still more preferably 39 contiguous nucleotides contained in the sequence given by the complement of SEQ ID NO:10. Preferred oligonucleotide sequences include RNA and DNA equivalents, and may include at least one nucleotide analog.

Introduction and Background

In the development of the invention, rRNA sequences from a collection of related and unrelated organisms were aligned to identify candidate sequences conserved within the genus Staphylococcus present in the 16S rRNA that could be used to distinguish Staphylococcus organisms from other bacterial and eukaryotic organisms. The procedures employed to make this discovery included examination of partial or complete sequences of the rRNA or rDNA of Staphylococcal organisms and unrelated phylogenetic neighbors, aligning the sequences to reveal areas of maximum homology and examining the alignment for regions with sequence variation in order to identify rRNA sequences that are conserved among members of the genus Staphylococcus but that exhibit mismatches with rRNA sequences of other closely and distantly related genera. The sequences deduced as candidate probes according to the methods described below finally were tested against a panel of rRNA standards and bacterial lysates to verify their utility as probes under laboratory conditions.

Polynucleotide sequences of rRNAs are most conveniently determined using a dideoxynucleotide sequencing procedure. In this procedure, oligonucleotide primers of about 10–100 bases in length and complementary to conserved regions of rRNA from any of the 5S, 16S or 23S ribosome subunits can be extended by reverse transcriptase. The resulting DNA extension products can then be sequenced either by chemical degradation or by dideoxynucleotide sequencing (Lane et al., *Proc. Natl. Acad. Sci. USA* 82: 6955 (1985)). According to another preferred method, genomic sequences encoding the rRNA can also be determined.

The strong interdependence of secondary structure and function of the rRNA molecules is well known. Indeed, evolutionary changes in the primary sequence of the rRNA are effectively restricted such that secondary structure of the molecule will be maintained. For example, if a base is changed on one side of a helix of a rRNA molecule, then a compensating change will be made on the other side of the helix to preserve complementarity (this is referred to as covariance). This relationship allows two very different rRNA sequences to be "aligned" based on conserved primary sequence and conserved elements of the secondary structure. Once the sequences have been aligned, it becomes possible to identify conserved and variable regions of the rRNA sequence.

Variable regions of rRNAs were identified by comparative analysis using published rRNA sequences and sequences that were determined during the development of the present invention. Commercially available software can be used or adapted for the purposes disclosed herein. Since the sequence evolution at each of the variable regions (for example, spanning a minimum of 10 nucleotides) of rRNA is, for the most part, divergent and not convergent, we can confidently design probes based on a few rRNA sequences which differ between the target organism and its phylogenetically closest relatives. Indeed, we have detected sufficient variation between the rRNA sequences of numerous target organisms and their closest phylogenetic relatives in a single sample to permit the design of a probe that can be used according to the methods described below.

Probe Selection Guidelines

The following general guidelines can be used for designing probes having desirable characteristics in accordance with the present invention. Manipulation of one or more of the many factors that influence the extent and specificity of a hybridization reaction can determine the sensitivity and specificity of a particular probe. This is true whether or not the probe is perfectly complementary over the full length of its target polynucleotide sequence. Guidelines for preparing probes useful in connection with the invention now follow.

First, the stability of the probe:target nucleic acid hybrid should be chosen to be compatible with the assay conditions. This may be accomplished by avoiding long A and T rich sequences, by terminating the hybrids with G:C base pairs and by designing the probe in such a way that the Tm will be appropriate for standard conditions to be employed in the assay. The nucleotide sequence of the probe should be chosen so that the length and %G and %C result in a probe having a Tm about 2–10° C. higher than the temperature at which the final assay will be performed. The base composition of the probe is significant because G:C base pairs exhibit greater thermal stability when compared with A:T base pairs. Thus, hybrids involving complementary nucleic acids having a high G:C content will be stable at higher temperatures when compared with hybrids having a lower G:C content.

Ionic strength and temperature conditions at which a hybridization reaction will be conducted also should be considered when designing a probe having a negatively charged backbone, such as would be provided by phosphodiester linkages between nucleotides. It is generally known that hybridization rate increases as ionic strength of the reaction mixture increases. Similarly, the thermal stability of hybrids increases with increasing ionic strength. Conversely, hydrogen bond-disrupting reagents such as formamide, urea, DMSO and alcohols increase the stringency of hybridization. Destabilization of the hydrogen bonds by reagents in this class can greatly reduce the Tm. In general, optimal hybridization for synthetic oligonucleotide probes of about 10–50 bases in length occurs approximately 5° C. below the melting temperature for a given duplex. Hybridization reactions conducted below the temperature optimum may allow mismatched base sequences to hybridize, and can result in reduced probe specificity.

Second, the position at which the probe binds its target polynucleotide should be chosen to minimize the stability of hybrids formed between probe:non-target polynucleotides. This may be accomplished by minimizing the length of perfect complementarity with polynucleotides of non-target organisms, by avoiding G:C rich regions of homology with non-target sequences, and by positioning the probe to span as many destabilizing mismatches as possible. Whether a probe sequence will be useful for detecting only a specific type of organism depends largely on thermal stability differences between probe:target hybrids and probe:non-target hybrids. The differences in Tm should be as large as possible to produce highly specific probes.

The length of the target nucleic acid sequence and the corresponding length of the probe sequence also are important factors to be considered when designing a probe useful for specifically detecting Staphylococcus. While it is possible for polynucleotides that are not perfectly complementary to hybridize to each other, the longest stretch of perfectly homologous base sequence will ordinarily be the primary determinant of hybrid stability.

Third, regions of the rRNA which are known to form strong internal structures inhibitory to hybridization of a probe are less preferred as targets. Probes having extensive self-complementarity also should be avoided. As indicated above, hybridization is the association of two single strands of complementary nucleic acid to form a hydrogen bonded double-stranded structure. If one of the two strands is wholly or partially double-stranded, then it will be less able to participate in the formation of a new hybrid. Significantly, all rRNA molecules form very stable intramolecular hybrids.

The rate and extent of hybridization between a probe and its target can be increased substantially by designing the probe such that a substantial portion of the sequence of interest is single-stranded. If the target nucleic acid to be detected is a genomic sequence encoding a rRNA, then that target will naturally occur in a double-stranded form. This is also the case with products of the polymerase chain reaction (PCR). These double-stranded targets are naturally inhibitory to hybridization with a probe. Finally, undesirable intramolecular and intermolecular hybrids can form within a single probe molecule or between different probe molecules if there is sufficient self-complementarity. Thus, extensive self-complementarity in a probe sequence should be avoided.

Preferably, probes useful for carrying out the procedures described below will hybridize only under conditions of high stringency. Under these conditions only highly complementary nucleic acid hybrids will form (i.e., those having at least 14 out of 17 bases in a contiguous series of bases being complementary). Hybrids will not form in the absence of a sufficient degree of complementarity. Accordingly, the stringency of the assay conditions determines the amount of complementarity needed between two nucleic acid strands forming a hybrid. Stringency is chosen to maximize the difference in stability between the hybrid formed with the target and non-target nucleic acid. Exemplary high stringency conditions are employed in the Examples presented below.

While oligonucleotide probes of different lengths and base composition may be used for detecting Staphylococcus, preferred probes in this invention have lengths of up to 100 nucleotides, and more preferably have lengths of up to 60 nucleotides. Preferred length ranges for the invented oligonucleotides are from 10 to 100 bases in length, or more preferably between 15 and 50 bases in length, and are sufficiently homologous to the target nucleic acid to permit hybridization under high stringency conditions, such as those employed in the Examples described below. However, the specific probe sequences described below also may be provided in a nucleic acid cloning vector or transcript or other longer nucleic acid and still can be used for detecting members of the genus Staphylococcus.

Chemical Structure of Oligonucleotides

All of the oligonucleotides of the present invention may be modified with chemical groups to enhance their performance. Thus, it is to be understood that references to "oligonucleotide probes" or "helper oligonucleotides" or simply "oligonucleotides" embrace polymers of native nucleotides as well as polymers that include at least one nucleotide analog.

Backbone-modified oligonucleotides, such as those having phosphorothioate or methylphosphonate groups, are examples of analogs that can be used in conjunction with oligonucleotides of the present invention. These modifications render the oligonucleotides resistant to the nucleolytic activity of certain polymerases or to nuclease enzymes. Other analogs that can be incorporated into the structures of the oligonucleotides disclosed herein include peptide nucleic acids, or "PNAs." The PNAs are compounds comprising ligands linked to a peptide backbone rather than to a phosphodiester backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker. The PNAs are able to bind complementary ssDNA and RNA strands. Methods for making and using PNAs are disclosed in U.S. Pat. No. 5,539,082. Another type of modification that can be used to make oligonucleotides having the sequences described herein involves the use of non-nucleotide linkers (e.g., Arnold, et al., "Non-Nucleotide Linking Reagents for Nucleotide Probes", U.S. Pat. No. 6,031,091 hereby incorporated by reference) incorporated between nucleotides in the nucleic acid chain which do not interfere with hybridization or the elongation of a primer.

Nucleic Acid Based Methods of Detecting rRNA or rDNA

A composition that includes an oligonucleotide probe, either alone or in combination with one or more helper oligonucleotides, can be used for detecting rRNA or rDNA of bacteria that are members of the genus Staphylococcus in a hybridization assay. Defined oligonucleotides that can be used to practice the invention can be produced by any of several well-known methods, including automated solid-phase chemical synthesis using cyanoethylphosphoramidite precursors (Barone et al., *Nucl Acids Res* 12:4051 (1984)). Other well-known methods for preparing synthetic oligonucleotides also can be employed.

Essentially any labeling and detection system that can be used for monitoring specific nucleic acid hybridization can be used in conjunction with the probes disclosed herein when a labeled probe is desired. Included among the collection of useful labels are: isotopic labels, enzymes, haptens, linked oligonucleotides, chemiluminescent molecules and redox-active moieties that are amenable to electrochemical detection methods. Standard isotopic labels that can be used to produce labeled oligonucleotides include $^3$H, $^{35}$S, $^{32}$P, $^{125}$I, $^{57}$Co and $^{14}$C. When using radiolabeled probes, hybrids can be detected by autoradiography, scintillation counting or gamma counting.

Non-isotopic materials can also be used for labeling oligonucleotide probes. These non-isotopic labels can be positioned internally or at a terminus of the oligonucleotide probe. Modified nucleotides can be incorporated enzymatically or chemically with modifications of the probe being performed during or after probe synthesis, for example, by the use of non-nucleotide linker groups. Non-isotopic labels include fluorescent molecules, chemiluminescent molecules, enzymes, cofactors, enzyme substrates, haptens or other ligands. Acridinium esters are particularly preferred non-isotopic labels useful for detecting probe hybrids.

Indeed, any number of different non-isotopic labels can be used for preparing labeled oligonucleotides in accordance with the invention. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. U.S. Pat. 5,998,135 discloses yet another method that can be used for labeling and detecting the probes of the present invention using fluorimetry to detect fluorescence emission from lanthanide metal labels disposed on probes, where the emission from these labels becomes enhanced when it is in close proximity to an energy transfer partner. Preferred electrochemical labeling and detection approaches are disclosed in U.S. Pat. Nos. 5,591,578 and 5,770,369, and the published International Pat. Application PCT/US98/12082, the disclosures of which are hereby incorporated by reference. Redox active moieties useful as electrochemical labels in the present invention include transition metals such as Cd, Mg, Cu, Co, Pd, Zn, Fe and Ru.

Those having an ordinary level of skill in the art will appreciate that alternative procedures for detecting Staphylococcal bacteria using the invented probes can be carried out using either labeled probes or unlabeled probes. For example, hybridization assay methods that do not rely on the use of a labeled probe are disclosed in U.S. Pat. No. 5,945,286 which describes immobilization of unlabeled probes made of peptide nucleic acids (PNAs), and detectably labeled intercalating molecules which can bind double-stranded PNA probe/target nucleic acid duplexes. In these procedures, as well as in certain electrochemical detection procedures, such as those disclosed in published International Patent No. Application No. PCT/US98/12082 entitled "Detection of Analytes Using Reorganization Energy," published International Patent Application No. PCT/US98/12430 entitled "Electronic Methods for the Detection of Analytes," and in published International Patent Application No. PCT/US97/20014 entitled "Electrodes Linked Via Conductive Oligomers to Nucleic Acids" the oligonucleotide probe is not required to harbor a detectable label.

Acceptability of the final product following synthesis and purification of an oligonucleotide may be verified by any of several procedures. First, polyacrylamide gel electrophoresis can be used to determine the size and purity of the oligonucleotide according to standard laboratory methods (see *Molecular Cloning: A Laboratory Manual*, Sambrook et al., eds. Cold Spring Harbor Lab Publ., 11.51, (1989)). Alternatively, High Pressure Liquid Chromatography ("HPLC") procedures can be used for this same purpose.

Hybridization between the labeled oligonucleotide probe and target nucleic acid in the procedures described below can be enhanced through the use of unlabeled "helper oligonucleotides" according to the procedure disclosed by Hogan et al., in U.S. Pat. No. 5,030,557 entitled, "Means and Methods for Enhancing Nucleic Acid Hybridization." As indicated above, helper oligonucleotides bind a region of the target nucleic acid other than the region that is bound by the assay probe. This binding imposes new secondary and tertiary structures on the targeted region of the single-stranded nucleic acid and accelerates the rate of probe binding. Helper oligonucleotides which can be used in combination with labeled oligonucleotide probes of the present invention are preferably 17 to 100 nucleotides in length and have a sequence that includes at least 17 contiguous nucleotides contained within the sequence of SEQ ID NO:10. Other preferred helper oligonucleotides have lengths of up to 100 nucleotides and include at least 39 contiguous nucleotides contained within the sequence of SEQ ID NO:10.

Those having an ordinary level of skill in the art will appreciate that factors affecting the thermal stability of a probe:target hybrid also can influence probe specificity. Accordingly, the melting profile, including the melting temperature (Tm) of probe:target hybrids, should be empirically determined for each probe:target combination. A preferred method for making this determination is described by Arnold et al., in U.S. Pat. No. 5,283,174, entitled "Homogeneous Protection Assay."

One approach for measuring the Tm of a probe:target hybrid involves conducting a hybridization protection assay. According to the method of this assay, a probe:target hybrid is formed under conditions of target excess in a lithium succinate buffered solution containing lithium lauryl sulfate. Aliquots of the "preformed" hybrids are diluted in the hybridization buffer and incubated for five minutes at various temperatures starting below the anticipated Tm (typically 55° C.) and increasing in 2–5 degree increments. This solution is then diluted with a mildly alkaline borate buffer and incubated at a lower temperature (for example 50° C.) for ten minutes. An acridinium ester (AE) linked to a single-stranded probe will be hydrolyzed under these conditions while an acridinium ester linked to a hybridized probe will be relatively "protected." This procedure is referred to as the hybridization protection assay ("HPA"). The amount of chemiluminescence remaining is proportional to the amount of hybrid and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In an alternative approach, the Tm of a probe:target hybrid can be determined using an isotopically labeled probe. In all cases, the Tm for a given hybrid will vary depending on the concentration of salts, detergents and other solutes contained in the hybridization solution. All of these factors influence relative hybrid stability during thermal denaturation (*Molecular Cloning: A Laboratory Manual* Sambrook et al., eds. Cold Spring Harbor Lab Publ., 9.51 (1989)).

The rate at which a probe hybridizes to its target is a measure of the thermal stability of the target secondary structure in the probe region, and can be can be determined using $C_0t_{1/2}$ measurements. These kinetic measurements of hybridization rate have units of (moles of nucleotide per liter)×(seconds). Expressed more simply, the $C_0t_{1/2}$ value is the concentration of probe times the half-life of hybridization at that concentration. This value can be determined by hybridizing various amounts of probe to a constant amount of target nucleic acid for a fixed time. For example, 0.05 pmol of target is incubated with 0.012, 0.025, 0.05, 0.1 and 0.2 pmol of probe for 30 minutes. The $C_0t_{1/2}$ may also be determined by hybridizing the target and probe under conditions of target excess and then measuring the increase of duplex formation over time. The amount of hybrid present can be measured using the above-described BPA procedure or by scintillation counting, if a radiolabeled probe is used in the procedure. The measured signal, when using AE labeled probe, is then plotted as the log of the percent of maximum Relative Light Units ("RLU") from the highest probe concentration versus probe concentration (moles of nucleotide per liter). The $C_0t_{1/2}$ is graphically determined from the concentration corresponding to 50% of maximum hybridization multiplied by the hybridization time in seconds. These values range from $9\times10^{-6}$ to $9\times10^{-5}$ with the preferred values being less than 3.5×10−5. Similar values may be obtained by measuring radioactivity and plotting % hybridization at a given time point vs. maximum extent.

In a preferred method of determining whether a biological sample contains rRNA or rDNA that would indicate the presence of members of the Staphylococcus genus, nucleic acids can be released from bacterial cells by sonic disruption, for example according to the method disclosed by Murphy et al., in U.S. Pat. No. 5,374,522. Other known methods for disrupting cells include the use of enzymes, osmotic shock, chemical treatment, and vortexing with glass beads. Other methods suitable for liberating from microorganisms the nucleic acids that can be subjected to the hybridization methods disclosed herein have been described by Clark et al., in U.S. Pat. No. 5,837,452 and by Kacian et al., in U.S. Pat. No. 5,5,364,763. Following or concurrent with the release of rRNA, labeled probe may be added in the presence of accelerating agents and incubated at the optimal hybridization temperature for a period of time necessary to a achieve significant hybridization reaction.

The following polynucleotide sequence was characterized by the criteria of length, Tm and nucleotide sequence and was found to be specific for the rRNA of bacteria in the genus Staphylococcus: (SauA1276) CCGAACTGAGAA-CAACTTTATGGGATTTGC (SEQ ID NO:1). This sequence is complementary to a unique segment found in the 16S rRNA of all Staphylococcus organisms. A representative list of bacteria within the Staphylococcus genus can be found in Table 2. The probe is 30 bases in length, has an RXL linker between 19 and nucleotides from the 5' end and has a Tm of 60.2° C., and hybridized rRNA of *Staphylococcus aureus* in a region corresponding to bases 1276–1305 of *E. coli* 16S rRNA.

This probe is one illustration of an oligonucleotide that: (1) hybridizes the target nucleic acid under high stringency hybridization conditions, (2) has a length of up to 100 nucleotide bases, and (3) includes at least 17, or more preferably at least 30, contiguous nucleotides falling within the 1276–1344 target region identified by SEQ ID NO:10 or its complement. Other oligonucleotides having these properties are contemplated for use as hybridization assay detection probes and are embraced by the invention.

Similarly, oligonucleotides having the sequences of SEQ ID NOs:2 and 3 are disclosed herein as illustrations of useful helper oligonucleotides. Like the helper oligonucleotides employed in the working Examples herein, other helper oligonucleotides embraced by the invention also have sequences of up to 100 nucleotides in length and further have at least 17 contiguous nucleotides contained within the target region identified by SEQ ID NO:10 or its complement.

As indicated below, the SauA1276 probe hybridized *Staphylococcus aureus* rRNA in a manner that was promoted by the use of helper oligonucleotides. According to the procedure used to make this determination, a single-stranded probe oligonucleotide radiolabeled at the 5'-end was contacted with rRNA from *Staphylococcus aureus* in the presence or absence of helper oligonucleotides. Probe molecules hybridizing the rRNA to form double-stranded hybrids were separated from single-stranded probe molecules by hydroxyapatite capture. The double-stranded hybrids bound to the hydroxyapatite and were detected and quantitated by scintillation counting. The extent of hybridization was then calculated as a percentage. As indicated below, the Tm of the probe:target hybrid advantageously was increased in the presence of one or more helper oligonucleotides.

The following Example describes the methods used to demonstrate that the SauA1276 probe hybridized rRNA from Staphylococcus aureus and that this interaction was facilitated by including helper oligonucleotides in the hybridization mixture.

EXAMPLE 1

Tm Determination for Probe:Target Hybrids

Tm values for probe:target and helper:target hybrids were determined using an end-labeled probe having the sequence of SauA1276 and end-labeled helper oligonucleotides selected from the group: (A) OMe SauA1259 and (B) SauA1306. The sequence of SauA1276 is CCGAACT-GAGAACAACTTTATGGGATTTGC (SEQ ID NO:1), the sequence of OMe SauA1259 is UUGACCUCGCGGU-UUCG (SEQ ID NO:2) and the sequence of SauA1306 is GCGATTCCAGCTTCATGTAGTCGAGTTG-CAGACTACAAT (SEQ ID NO:3). Helpers A and B were selected to bind the rRNA of Staphylococcal organisms in regions of the molecule immediately adjacent to the probe, helper A binding in about the 1259–1275 region of the 16S rRNA, and helper B binding in the 1306–1344 region of the 16S rRNA. The probe and helper oligonucleotides were 5'-end labeled using $\gamma$-$^{32}$P]ATP as a phosphate donor and T4 polynucleotide kinase to catalyze the phosphate transfer reaction essentially as described in *Molecular Cloning: A Laboratory Manual* (Sambrook et al., eds. Cold Spring Harbor Lab Publ. 10.59 (1989)). End-labeled oligonucleotides were separately combined with purified rRNA from *Staphylococcus aureus* to provide conditions of target excess. In trials that included both the probe and helper oligonucleotides, only the probe was end-labeled and each helper oligonucleotide was present in a 10 fold molar excess over the target. All mixtures were hybridized to completion in a solution that included 0.48 M sodium phosphate buffer, 0.1% sodium dodecyl sulfate, 1 mM EDTA and 1 mM EGTA. As negative controls, the probe and/or helper oligonucleotides were hybridized in the absence of the nucleic acid target. At the conclusion of the hybridization procedure, mixtures were diluted and passed over a hydroxyapatite column to separate single-stranded nucleic acids from double-stranded hybrids. The amount of radioactivity in the column flow-through represented single-stranded probe and was measured by scintillation counting. The amount of radioactivity bound to the hydroxyapatite was separately measured by scintillation counting. The extent of hybrid formation, expressed as a percentage, was calculated by dividing the amount of probe (measured in cpm) bound to the hydroxyapatite by the total amount of probe (in cpm) that was applied to the column. Results of these procedures are presented in Table 1.

TABLE 1

Hybridization of the SauA1276 Probe with Target rRNA

| | % Hybridization | Tm (° C.) |
|---|---|---|
| SauA1276 (Probe) | 75 | 60.2 |
| helper A (OMe SauA1259) | 94.2 | 76.8 |
| helper B (SauA1306) | 92.2 | 75.2 |
| Probe + helper A | 87.5 | 63 |
| Probe + helper B | 92.6 | 62.5 |
| Probe + helper A + helper B | 91.9 | 65.2 |

The results from this procedure confirmed that the end-labeled probe hybridized *Staphylococcus aureus* rRNA and that this interaction advantageously was facilitated by helper oligonucleotides. We particularly observed that the Tm of the probe:target complex could be increased from 60.2 up to 65.2° C. when helper oligonucleotides were included in the hybridization reaction. Although the probe can be used either alone or in combination with one or more helper oligonucleotides for hybridizing Staphylococcus rRNA, the below-described experiments to characterize the probe were conducted using the probe in combination with helper oligonucleotides having the sequences of OMe SauA1259 and SauA1306. Combinations of probe and helper oligonucleotides useful in the procedures described herein preferably have probe:target Tm values in the range of from about 62–66° C. under the conditions described above.

Probe specificity was confirmed by demonstrating positive hybridization to rRNAs from a specificity panel. The collection of organisms used as sources of target nucleic acids in this procedure represented a broad taxonomic cross-section of organisms and a nearest-neighbor group. In the following procedure, quantitative results using the AE-labeled hybridization probe were compared to the amount of bacterial rRNA present in each sample using a positive control probe. This positive control probe, which hybridized rRNA from all species of bacteria, was particularly useful for confirming the presence of bacterial rRNA in samples that failed to hybridize Ad the SauA1276 probe. In such an event, the positive control probe provided confirmation for the presence of hybridizable rRNA and so validated the negative results. In the case of fungal rRNA targets, a broadly reactive fungal rRNA hybridization probe served as the positive control.

The following Example describes the methods used to demonstrate that the SauA1276 AE 19.20 probe hybridized rRNAs from a panel of Staphylococcus organisms

EXAMPLE 2

Verification of Probe Specificity

Bacterial lysates or purified RNA were used as nucleic acid targets for hybridization of a probe having the sequence of SauA1276 AE 19.20 together with helper oligonucleotides having the sequences of SauA1259 and SauA1306. Organisms employed as sources of rRNA in this procedure were either typed clinical isolates or obtained from the American Type Culture Collection (ATCC). All samples are identified in Table 2 by master log numbers for Gen-Probe Incorporated. Parallel samples of each rRNA were hybridized with a labeled positive control probe having the sequence CGACAAGGAAUUUCGC (OMe EcoB1933 AE 12.13) (SEQ ID NO:4) and unlabeled helper oligonucleotides having the sequences UACCUUAGGACCGUUAU (OMe EcoB1916) (SEQ ID NO:5) and CAGGUCG-GAACUUACC (OMe EcoB1949a) (SEQ ID NO:6). The hybridization solution contained 0.6M LiCl, 1% lithium lauryl sulfate, 60 mM lithium succinate and 10M of both EDTA and EGTA, pH 5.5. Both the SauA1276 probe and the positive control probe were labeled with acridinium ester essentially according to the method disclosed in U.S. Pat. No. 5,185,439, entitled "Acridinium Ester Labeling and Purification of Nucleotide Probes." At the conclusion of the hybridization reaction, acridinium ester linked to unhybridized probe was rendered non-chemiluminescent under mild alkaline conditions, while acridinium ester attached to hybridized probe remained resistant to the inactivation. Conditions for the hydrolysis and detection of hybridized probe labeled with acridinium ester are described by Arnold et al., in Clin. Chem. 35:1588 (1989)). The magnitudes of probe hybridization in these procedures were quantitated by luminometry using procedures familiar to those having ordinary skill in the art. The magnitude of the Staphylococcus genus probe signal was then divided by the magnitude of the bacterial positive control signal to quantitatively normalize results in the study. Samples having SauA1276 AE 19.20 probe signals that were greater than 30% of the positive control signal indicated specific hybridization with the SauA1276 AE probe with helpers, while lower values indicated negative results for this assay format. Results of the assay are shown in Table 2.

TABLE 2

Hybridization of the SauA1276 Probe and rRNA-Containing Lysates from a Collection of Staphylococcus Species

| | | Hybridization Results | | |
|---|---|---|---|---|
| GP#* | rRNA Source (Organism) | Pan-Bacterial Probe (RLU) | Staphylococcus Probe (RLU) | Fractional Hybridization (%) |
| 49 | Staphylococcus aureus | 5286 | 23717 | 449 |
| 63 | Staphylococcus Cohnii | 5544 | 14621 | 264 |
| 6 | Staphylococcus Delphi | 5917 | 23431 | 396 |
| 50 | Staphylococcus epidermidis | 7754 | 30347 | 391 |
| 62 | Staphylococcus haemolyticus | 4645 | 23331 | 502 |
| 61 | Staphylococcus hominis | 4884 | 23381 | 479 |
| 69 | Staphylococcus hyicus | 5484 | 27551 | 502 |
| 60 | Staphylococcus intermedius | 6823 | 24677 | 362 |
| 59 | Staphylococcus saprophyticus | 3484 | 10116 | 290 |
| 39 | Staphylococcus simulans | 5890 | 19007 | 323 |
| 67 | Staphylococcus warneri | 3565 | 14881 | 417 |

*"GP#" entries indicate master log numbers for Gen-Probe Incorporated.

The results presented in Table 2 confirmed that the probe directed against Staphylococcus rRNA efficiently hybridized rRNA samples from numerous Staphylococcal species.

Specificity of the probe directed against rRNA of the genus Staphylococcus was further investigated by hybridizing the labeled probe with rRNAs from a collection of species representing a broad spectrum of phylogenetically diverse organisms. In this procedure, AE-labeled probe was separately mixed with purified rRNA or rRNA-containing lysates from organisms that were only phylogenetically distantly related to the genus Staphylococcus. Positive hybridization results obtained using the positive control probe and negative results obtained using the SauA1276 probe in the following procedure further indicated that the SauA1276 probe was highly specific for the genus Staphylococcus.

The following Example describes additional methods used to demonstrate specificity of the probe. More particularly, the following procedures showed that the SauA1276 probe did not cross hybridize with lysates from phylogenetically distantly related organisms.

EXAMPLE 3

Absence of Cross Hybridization with Phylogentically Unrelated Organisms

Hybridization assays were conducted using the AE-labeled probe and helper oligonucleotides according to the procedures described in the previous Example except that lysates containing rRNA isolated from numerous diverse species served as target nucleic acids. Results of the procedure are presented in Table 3. A pan-fungal probe having the sequence GTCTGGACCTGGTGAGTTTCCC (SEQ ID NO:7), and helper oligonucleotides having the sequences CGUGUUGAGUCAAAUUAAGCCGC (SEQ ID NO:8) and GCUCUCAAUCUGUCAAUCCUAUUGU (SEQ ID NO:9) were used as positive controls to detect fungal rRNAs. Results obtained using a collection of fungal organisms are presented in Table 4.

TABLE 3

Hybridization of the SauA1276 Probe with rRNA from a Collection of Phylogenetically Non-Related Organisms

| GP#* | rRNA Source (Organism) | Pan-Bacterial Probe (RLU) | SauA1276 AE Probe (RLU) | Fractional Hybridization (%) |
|---|---|---|---|---|
| 234 | Acinetobacter calcoaceticus | 3784 | 0 | 0 |
| 233 | Acinetobacter lwoffi | 3914 | 83 | 2 |
| 13 | Bacillus brevis | 8615 | 118 | 1 |
| 11 | Bacillus subtilis | 4506 | 155 | 3 |
| 212 | Bacteriodes fragilis | 7165 | 541 | 8 |
| 226 | Bacteroides ovatus | 3676 | 254 | 7 |
| 225 | Bacteroides thetaiotamicron | 32979 | 118 | 0 |
| 152 | Citrobacter diversus | 6126 | 203 | 3 |
| 150 | Citrobacter freundii | 8479 | 326 | 4 |
| 192 | Clostridium perfringens | 7144 | 0 | 0 |
| 236 | Corynebacterium aquaticum | 19019 | 132 | 1 |
| 239 | Corynebacterium jeikieum | 8827 | 180 | 2 |
| 237 | Corynebacterium xerosis | 8776 | 190 | 2 |
| 153 | Enterobacter aerogenes | 7597 | 478 | 6 |
| 154 | Enterobacter agglomerans | 8044 | 81 | 1 |
| 155 | Enterobacter cloacae | 7441 | 252 | 3 |
| 215 | Enterobacter fragilis | 6467 | 50 | 1 |
| 156 | Enterobacter gergoviae | 2729 | 405 | 15 |
| 46 | Enterococcus avium | 9135 | 33 | 0 |
| 27 | Enterococcus casseliflavus | 9661 | 316 | 3 |
| 7 | Enterococcus cecorum | 5233 | 466 | 9 |
| 15 | Enterococcus dispar | 8492 | 233 | 3 |
| 85 | Enterococcus durans | 8130 | 221 | 3 |
| 82 | Enterococcus faecalis | 7201 | 797 | 11 |
| 79 | Enterococcus faecium | 6987 | 0 | 0 |
| 23 | Enterococcus faecium V1 | 4929 | 0 | 0 |
| 17 | Enterococcus faecium V6 | 5083 | 798 | 16 |
| 89 | Enterococcus gallinarum | 7973 | 277 | 3 |
| 81 | Enterococcus hirae | 5429 | 198 | 4 |
| 45 | Enterococcus malodoratus | 14729 | 52 | 0 |
| 25 | Enterococcus mundtii | 8804 | 575 | 7 |
| 26 | Enterococcus pseudoavium | 9364 | 254 | 3 |
| 33 | Enterococcus raffinosus | 5984 | 127 | 2 |
| 47 | Enterococcus sacchrolyticus | 8339 | 0 | 0 |
| 159 | Escherichia coli | 5141 | 306 | 6 |
| 161 | Escherichia fergusonii | 4152 | 602 | 14 |
| 162 | Escherichia hermanii | 2821 | 317 | 11 |
| 217 | Haemophilus influenzae | 3726 | 191 | 5 |
| 219 | Haemophilus influenzae A | 3751 | 248 | 7 |
| 220 | Haemophilus influenzae B | 3816 | 182 | 5 |
| 222 | Haemophilus parainfluenzae | 24669 | 233 | 1 |
| 188 | Hafnia alvei | 47098 | 358 | 1 |
| 163 | Klebsiella oxytoca | 2642 | 289 | 11 |
| 164 | Klebsiella ozaenae | 4806 | 132 | 3 |
| 176 | Klebsiella pneumoniae | 4185 | 70 | 2 |
| 178 | Klebsiella rhinosclero | 3121 | 174 | 6 |
| 36 | Lactobacillus acidophilus | 20052 | 636 | 3 |
| 56 | Lactobacillus jensenii | 5863 | 1451 | 25 |
| 9 | Lactococcus lactis | 36172 | 74 | 0 |
| 41 | Listeria grayi | 2278 | 139 | 6 |
| 72 | Listeria ivanovii | 5646 | 316 | 6 |
| 31 | Listeria monocytogenes ½b | 9424 | 24 | 0 |
| 28 | Listeria monocytogenes 4b | 7547 | 153 | 2 |
| 73 | Listeria seeligeri | 6292 | 97 | 2 |
| 40 | Listeria welshimeri | 4610 | 798 | 17 |
| 240 | Micrococcus luteus | 1712 | 56 | 3 |
| 184 | Morganella morganii | 3406 | 262 | 8 |
| 196 | Neisseria gonorrhoea | 6152 | 169 | 3 |
| 198 | Neisseria meningitidis | 19758 | 137 | 1 |
| 191 | Peptostreptococcus anaerobius | 6313 | 485 | 8 |
| 190 | Propionibacterium acnes | 5008 | 556 | 11 |
| 179 | Proteus mirabilis | 4669 | 38 | 1 |
| 183 | Proteus penneri | 3607 | 170 | 5 |
| 181 | Proteus vulgaris | 5621 | 46 | 1 |
| 186 | Providencia alcalifaciens | 43548 | 449 | 1 |
| 187 | Providencia rettgeri | 30678 | 470 | 2 |
| 185 | Providencia stuartii | 13480 | 151 | 1 |
| 200 | Pseudomonas aeruginosa | 5099 | 565 | 11 |
| 203 | Pseudomonas cepacia | 24918 | 353 | 1 |
| 205 | Pseudomonas fluorescens | 8004 | 505 | 6 |
| 206 | Pseudomonas maltophilia | 7031 | 478 | 7 |
| 209 | Pseudomonas mendocina | 17308 | 151 | 1 |
| 208 | Pseudomonas pickettii | 7282 | 551 | 8 |
| 210 | Pseudomonas putida A | 7544 | 599 | 8 |
| 211 | Pseudomonas stutzeri | 7100 | 420 | 6 |
| 189 | Salmonella enteritidis | 20228 | 2166 | 11 |
| 216 | Salmonella paratyphi | 3822 | 273 | 7 |
| 165 | Salmonella typhi | 7326 | 126 | 2 |
| 166 | Salmonella typhimurium | 5119 | 102 | 2 |
| 170 | Serratia liquefaciens | 5355 | 532 | 10 |
| 171 | Serratia marcescens | 4647 | 380 | 8 |
| 168 | Shigella dysenteriae | 4787 | 263 | 5 |
| 169 | Shigella sonnei | 4675 | 355 | 8 |
| 53 | Streptococcus agalactiae | 6617 | 949 | 14 |
| 32 | Streptococcus agalactiae 1a | 9466 | 348 | 4 |
| 43 | Streptococcus anginosus | 8183 | 189 | 2 |
| 16 | Streptococcus avium | 5688 | 74 | 1 |
| 34 | Streptococcus bovis | 8620 | 41 | 0 |
| 51 | Streptococcus equi | 12255 | 651 | 5 |
| 80 | Streptococcus equinus | 4550 | 275 | 6 |
| 37 | Streptococcus equisimilis | 7445 | 517 | 7 |
| 97 | Streptococcus grp C | 8552 | 356 | 4 |
| 98 | Streptococcus grp G | 6769 | 182 | 3 |
| 44 | Streptococcus mutans | 6196 | 394 | 6 |
| 42 | Streptococcus pneumoniae | 5475 | 142 | 3 |
| 91 | Streptococcus pyogenes | 5707 | 215 | 4 |
| 92 | Streptococcus pyogenes | 6082 | 61 | 1 |
| 38 | Streptococcus salivarius | 7366 | 622 | 8 |
| 35 | Streptococcus sanguis | 11240 | 293 | 3 |
| 66 | Streptococcus sp gp F2 | 6212 | 363 | 6 |
| 3 | Streptococcus sp. Gp. B, II | 5476 | 329 | 6 |
| 5 | Streptococcus uberis | 5389 | 247 | 5 |
| 173 | Yersinia enterocolitica | 5719 | 371 | 6 |
| 175 | Yersinia intermedia | 4800 | 0 | 0 |
| 174 | Yersinia pseudotuberculosis | 5118 | 178 | 3 |

*"GP#" entries indicate master log numbers for Gen-Probe Incorporated.

TABLE 4

Hybridization of the SauA1276 Probe with rRNA from a Collection of Fungal Organisms

| GP#* | rRNA Source (Organism) | Pan-Bacterial Probe (RLU) | Staph Genus Probe (RLU) | Pan-Fungal Probe (RLU) | Hybrid (%) |
|---|---|---|---|---|---|
| F-932 | Arachnoitus flavoluteus | 481 | 684 | 232076 | 0.3 |
| F-906 | Aspergillus flavus | 364 | 674 | 348387 | 0.2 |
| F-899 | Aspergillus fumigatus | 382 | 676 | 419831 | 0.2 |
| F-907 | Aspergillus niger | 194 | 572 | 650747 | 0.1 |
| F-930 | Auxarthron thaxteri | 301 | 638 | 494055 | 0.1 |
| F-1022 | Blastomyces dermatitidis | 296 | 569 | 422465 | 0.1 |
| 715 | Candida albicans | 369 | 571 | 327951 | 0.2 |
| 1123 | Candida glabrata | 1419 | 2219 | 45039 | 4.9 |
| 717 | Candida parapsilosis | 352 | 1318 | 312482 | 0.4 |
| 1091 | Candida tropicalis | 1566 | 2199 | 24023 | 9.2 |
| F-1399 | Coccidioides immitis | 303 | 958 | 141956 | 0.7 |

TABLE 4-continued

Hybridization of the SauA1276 Probe with rRNA from a Collection of Fungal Organisms

| GP#* | rRNA Source (Organism) | Pan-Bacterial Probe (RLU) | Staph Genus Probe (RLU) | Pan-Fungal Probe (RLU) | Hybrid (%) |
|---|---|---|---|---|---|
| F-900 | Cryptococcus neoformans | 316 | 998 | 452943 | 0.2 |
| F-965 | Gymnoascus dugwayenis | 317 | 700 | 506033 | 0.1 |
| F-968 | Histoplasma capsulatum | 254 | 794 | 346283 | 0.2 |
| F-933 | Myxotrichum deflexum | 267 | 648 | 366688 | 0.2 |
| F-934 | Oidiodendron ecinulatum | 238 | 746 | 322685 | 0.2 |
| 716 | Candida krusei | 669 | 318 | 71371 | 0.4 |
| 1087 | Candida pseudotropicalis | 243 | 112 | 79868 | 0.1 |
| 384 | Saccharomyces cerevisiae | 116 | 233 | 75954 | 0.3 |
| 1080 | Candida guilliermondii | 320 | 607 | 65011 | 0.9 |

*"GP#" identifies organisms by master log numbers for Gen-Probe Incorporated.

The results presented in Table 3 confirmed that the probe did not cross hybridize with the rRNA of numerous phylogentically diverse bacterial species. The results in Table 4 show that the probe did not cross-hybridize with the rRNA of fungal species. Taken together with the positive hybridization results presented in the Table 2, it was clear that the hybridization probe was highly specific for rRNA of the genus Staphylococus.

The results presented above confirmed that the novel probes disclosed herein were capable of detecting Staphylococcus organisms. Moreover, the probes were capable of distinguishing Staphylococcus from organisms that were phylogenetically closely related.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A probe composition for detecting nucleic acids of bacteria that are members of the Staphylococcus genus, comprising:
   an oligonucleotide probe that hybridizes under a high stringency condition to a Staphylococcal 16S rRNA or rDNA to form a detectable probe:target duplex,
   wherein said oligonucleotide probe has the length and sequence of SEQ ID NO:1 or the complement thereof, and optionally a non-complementary sequence that does not hybridize to said Staphylococcal 16S rRNA or rDNA, and
   wherein under said hybridization condition said oligonucleotide probe hybridizes to nucleic acids present in *Staphylococcus aureus, Staphylococcus cohnii, Staphylococus delphi, Staphylococcus epidermidis, Staphylococcus haemolyticus, Staphylococcus hominis, Staphylococcus hyicus, Staphylococcus intermedius, Staphylococcus saprophyticus, Staphylococcus simulan* and *Staphylococcus warneri*.

2. The probe composition of claim 1, wherein the oligonucleotide probe comprises DNA.

3. The probe composition of claim 1, wherein said high stringency condition comprises 0.48 M sodium phosphate buffer, 0.1% sodium dodecyl sulfate, and 1 mM each of EDTA and EGTA.

4. The probe composition of claim 1 wherein said high stringency condition comprises 0.6 M LiCl, 1% lithium lauryl sulfate, 60 mM lithium succinate and 10 mM each of EDTA and EGTA.

5. The probe composition of claim 1, wherein said oligonucleotide probe has the length and sequence of SEQ ID NO:1.

6. The probe composition of claim 1, wherein said oligonucleotide probe further comprises a detectable label.

7. The probe composition of claim 5, wherein said oligonucleotide probe further comprises a detectable label.

8. The probe composition of claim 6 or claim 7 wherein the detectable label is a chemiluminescent label or a radioactive label.

9. The probe composition of claim 8, wherein the detectable label is a chemiluminescent label, and wherein the chemiluminescnect label is an acridinium ester.

10. The probe composition of claim 8, further comprising at least one helper oligonucleotide.

11. The probe composition of claim 10, wherein said at least one helper oligonucleotide includes at least one nucleotide analog.

12. The probe composition of claim 11, wherein said at least one nucleotide analog comprises a ribose moiety having a methoxy group disposed at the 2' position.

13. The probe composition of claim 10, wherein said at least one helper oligonucleotide has a sequence selected from the group consisting of SEQ ID NO:2 and SEQ ID NO:3.

14. A method for detecting the presence of Staphylococcus bacteria in a test sample, comprising the steps of:
   (a) providing to said test sample a probe composition that includes an oligonucleotide probe that hybridizes under a high stringency condition to a Staphylococcal 16S rRNA or rDNA to form a detectable probe:target duplex, wherein said oligonucleotide probe has the length and sequence of SEQ ID NO:1 or the complement thereof, and optionally a non-complementary sequence that does not hybridize to said Staphylococcal 16S rRNA or rDNA, and wherein under said hybridization condition said oligonucleotide probe hybridizes to nucleic acids present in *Staphylococcus aureus, Staphylococcus cohnii, Staphylococcus delphi, Staphylococcus epidermidis, Staphylococcus haemolyticus, Staphylococcus hominis, Staphylococcus hyicus, Staphylococcus intermedius, Staphylococcus saprophyticus, Staphylococcus simulan* and *Staphylococcus warneri;*
   (b) hybridizing under said high stringency condition any nucleic acids from Staphylococcus bacteria that are present in the test sample with said probe composition to form a probe:target duplex; and
   (c) detecting said probe:target duplex of (b) as an indicator of the presence of Staphylococcus bacteria in the test sample.

15. The method of claim 14, wherein said test sample may comprise bacteria, and wherein before step (a) there is a step for releasing nucleic acids from any bacteria that may be present in said test sample.

16. The method of claim 14, wherein said test sample is a lysate.

17. The method of claim 14, wherein said high stringency condition comprises 0.48 M sodium phosphate buffer, 0.1% sodium dodecyl sulfate, and 1 mM each of EDTA and EGTA.

18. The method of claim 14, wherein said high stringency condition comprises 0.6 M LiCl, 1% lithium lauryl sulfate, 60 mM lithium succinate and 10 mM each of EDTA and EGTA.

19. The method of claim 14, wherein the oligonucleotide probe has the length and sequence of SEQ ID NO:1.

20. The method of claim 19, wherein the oligonucleotide probe comprises a detectable label.

21. The method of claim 20, wherein the detectable label is an acridinium ester, and wherein the detecting step comprises performing luminometry to detect any of said probe-:target duplex of (b).

22. The method of claim 20, wherein said probe composition further comprises at least one helper oligonucleotide that facilitates formation of the probe:target duplex of (b).

23. The method of claim 22, wherein said at least one helper oligonucleotide is selected from the group consisting of SEQ ID NO:2 and SEQ ID NO:3.

24. A kit for detecting in a test sample the presence of nucleic acids from bacteria that are members of the Staphylococcus genus, comprising:

(a) a probe composition that includes an oligonucleotide probe that hybridizes under a high stringency condition to a Staphylococcal 16S rRNA or rDNA to form a detectable probe:target duplex, wherein said oligonucleotide probe has the length and sequence of SEQ ID NO:1 or the complement thereof, and optionally a non-complementary sequence that does not hybridize to said Staphylococcal 16S rRNA or rDNA, and wherein under said hybridization condition said oligonucleotide probe hybridizes to nucleic acids present in *Staphylococcus aureus, Staphylococcus cohnii, Staphylococcus delphi, Staphylococcus epidermidis, Staphylococcus haemolyticus, Staphylococcus hominis, Staphylococcus hyicus, Staphylococcus intermedius, Staphylococcus saprophyticus, Staphylococcus simulan* and *Staphylococcus warneri*; and (b) printed instructions specifying, in order of implementation, steps to be followed for detecting nucleic acids from bacteria that are members of the Staphylococcus genus by detecting a complex between the oligonucleotide probe and a Staphylococcus nucleic acid target, wherein said probe composition and said printed instructions are in packaged combination.

25. The probe composition of claim 1, wherein said oligonucleotide probe includes said non-complementary sequence, and wherein said non-complementary sequence is selected from the group consisting of a promoter sequence, a restriction endonuclease recognition site, a sequence that confers a secondary structure, and a sequence that confers a tertiary structure.

* * * * *

SEQUENCE LISTING

<160> NUMBER OF SEQ ID NOS: 20

<210> SEQ ID NO 1
<211> LENGTH: 30
<212> TYPE: DNA
<213> ORGANISM: Staphylococcus genus

<400> SEQUENCE: 1
ccgaactgag aacaacttta tgggatttgc                                    30

<210> SEQ ID NO 2
<211> LENGTH: 17
<212> TYPE: RNA
<213> ORGANISM: Staphylococcus genus

<400> SEQUENCE: 2
uugaccucgc gguuucg                                                  17

<210> SEQ ID NO 3
<211> LENGTH: 39
<212> TYPE: DNA
<213> ORGANISM: Staphylococcus genus

<400> SEQUENCE: 3
gcgattccag cttcatgtag tcgagttgca gactacaat                          39

<210> SEQ ID NO 4
<211> LENGTH: 16
<212> TYPE: RNA
<213> ORGANISM: Pan-bacterial

<400> SEQUENCE: 4

```
cgacaaggaa uuucgc                                                    16

<210> SEQ ID NO 5
<211> LENGTH: 17
<212> TYPE: RNA
<213> ORGANISM: Pan-bacterial

<400> SEQUENCE: 5
uaccuuagga ccguuau                                                   17

<210> SEQ ID NO 6
<211> LENGTH: 16
<212> TYPE: RNA
<213> ORGANISM: Pan-bacterial

<400> SEQUENCE: 6
caggucggaa cuuacc                                                    16

<210> SEQ ID NO 7
<211> LENGTH: 22
<212> TYPE: DNA
<213> ORGANISM: Pan-fungal

<400> SEQUENCE: 7
gtctggacct ggtgagtttc cc                                             22

<210> SEQ ID NO 8
<211> LENGTH: 23
<212> TYPE: RNA
<213> ORGANISM: Pan-fungal

<400> SEQUENCE: 8
cguguugagu caaauuaagc cgc                                            23

<210> SEQ ID NO 9
<211> LENGTH: 26
<212> TYPE: RNA
<213> ORGANISM: Pan-fungal

<400> SEQUENCE: 9
gcucucaauc ugucaauccu uauugu                                         26

<210> SEQ ID NO 10
<211> LENGTH: 86
<212> TYPE: DNA
<213> ORGANISM: Staphylococcus genus

<400> SEQUENCE: 10
gcgattccag cttcatgtag tcgagttgca gactacaatc cgaactgaga a caactttat   60 gggatttgct tgacctcgcg gtttcg                                         86

<210> SEQ ID NO 11
<211> LENGTH: 86
<212> TYPE: RNA
<213> ORGANISM: Staphylococcus genus

<400> SEQUENCE: 11
cgaaaccgcg aggucaagca aaucccauaa aguuguucuc aguucggauu g uagucugca   60 acucgacuac augaagcugg aaucgc                                         86

<210> SEQ ID NO 12
```

<211> LENGTH: 92
<212> TYPE: RNA
<213> ORGANISM: S. epidermidis

<400> SEQUENCE: 12
agcgaaaccg cgaggucaag caaaucccau aaaguuguuc ucaguucgga u uguagucug    60 caacucgacu auaugaagcu ggaaucgcua gu                                   92

<210> SEQ ID NO 13
<211> LENGTH: 92
<212> TYPE: RNA
<213> ORGANISM: S. aureus

<400> SEQUENCE: 13
agcgaaaccg cgaggucaag caaaucccau aaaguuguuc ucaguucgga u uguagucug    60 caacucgacu acaugaagcu ggaaucgcua gu                                   92

<210> SEQ ID NO 14
<211> LENGTH: 92
<212> TYPE: RNA
<213> ORGANISM: E. coli

<400> SEQUENCE: 14
agcgaccucg cgagagcaag cggaccucau aaagugcguc guagccgga u uggagucug    60 caacucgacu ccaugaaguc ggaaucgcua gu                                   92

<210> SEQ ID NO 15
<211> LENGTH: 92
<212> TYPE: RNA
<213> ORGANISM: S. bovis

<400> SEQUENCE: 15 gcgagucgg ugacggcaag caaaucucuu aaagccaauc ucaguucgga uu guaggcug    60 caacucgccu acaugaaguc ggaaucgcua gu                                   92

<210> SEQ ID NO 16
<211> LENGTH: 92
<212> TYPE: RNA
<213> ORGANISM: S. pneumonia

<400> SEQUENCE: 16
cgcaagccgg ugacggcaag cuaaucucuu aaagccaguc ucaguucgga u uguaggcug    60 caacucgccu acaugaaguc ggaaucgcua gu                                   92

<210> SEQ ID NO 17
<211> LENGTH: 92
<212> TYPE: RNA
<213> ORGANISM: S. agalactiae

<400> SEQUENCE: 17
cgcaagccgg ugacggcaag cuaaucucuu aaagccaauc ucaguucgga u uguaggcug    60 caacucgccu acaugaaguc ggaaucgcua gu                                   92

<210> SEQ ID NO 18
<211> LENGTH: 92
<212> TYPE: RNA
<213> ORGANISM: S. sanguis

<400> SEQUENCE: 18
cgcaagccgg ugacggcaag cuaaucucug aaagccaguc ucaguucgga u uguaggcug    60

-continued

```
caacucgccu acaugaaguc ggaaucgcua gu                            92

<210> SEQ ID NO 19
<211> LENGTH: 100
<212> TYPE: RNA
<213> ORGANISM: S. cerevisiae

<400> SEQUENCE: 19
ggccgagagg ucuugguaau cuugugaaac uccgucgugc uggggauaga g cauuguaau    60 uauugcucuu caacgaggaa uuccuaguaa gcgcaaguca                   100

<210> SEQ ID NO 20
<211> LENGTH: 97
<212> TYPE: RNA
<213> ORGANISM: C. albicans

<400> SEQUENCE: 20
auaagccuug gccgagaggu cugggaaauc uugugaaacu ccgucgugcu g gggauagag    60 cauuguaauu guugcucuuc aacgaggaau uccuagu                      97
```